(12) United States Patent
Sacchi et al.

(10) Patent No.: US 10,534,093 B2
(45) Date of Patent: Jan. 14, 2020

(54) CIRCUIT ARRANGEMENT FOR ACQUISITION OF SIGNALS FROM AN APPARATUS FOR MEASURING BEAMS OF CHARGED PARTICLES FOR EXTERNAL RADIOTHERAPY

(71) Applicants: DE.TEC.TOR S.r.l., Turin (IT); Istituto Nazionale di Fisica Nucleare, Frascati (IT); Università degli Studi di Torino, Turin (IT)

(72) Inventors: Roberto Sacchi, Turin (IT); Giovanni Mazza, Turin (IT); Federico Fausti, Turin (IT)

(73) Assignees: DE.TEC.TOR S.r.l., Turin (IT); Instituto Nazionale di Fisica Nucleare, Frascati (IT); Universitá degli Studi di Torino, Turin (IT)

( * ) Notice: Subject to any disclaimer, the term of this patent is extended or adjusted under 35 U.S.C. 154(b) by 0 days.

(21) Appl. No.: 15/580,816

(22) PCT Filed: Jun. 9, 2016

(86) PCT No.: PCT/IB2016/053408
§ 371 (c)(1),
(2) Date: Dec. 8, 2017

(87) PCT Pub. No.: WO2016/199067
PCT Pub. Date: Dec. 15, 2016

(65) Prior Publication Data
US 2018/0164445 A1 Jun. 14, 2018

(30) Foreign Application Priority Data
Jun. 10, 2015 (IT) .................. 102015000022390

(51) Int. Cl.
*G01T 1/17* (2006.01)
*G01T 1/29* (2006.01)
(Continued)

(52) U.S. Cl.
CPC .............. *G01T 1/17* (2013.01); *A61N 5/1071* (2013.01); *G01T 1/29* (2013.01); *A61N 2005/1087* (2013.01); *G01T 1/185* (2013.01)

(58) Field of Classification Search
CPC .. G01T 1/17; G01T 1/29; G01T 1/185; A61N 5/1071; A61N 2005/1087
See application file for complete search history.

(56) References Cited

U.S. PATENT DOCUMENTS

| | | | | |
|---|---|---|---|---|
| 5,619,034 A | * | 4/1997 | Reed .................. | H01J 49/025 250/286 |
| 2006/0051290 A1 | * | 3/2006 | Wilson ............... | A61K 49/1884 424/1.11 |
| 2010/0123483 A1 | * | 5/2010 | Chung ............... | G01R 31/3004 327/63 |

FOREIGN PATENT DOCUMENTS

WO WO 2007/141388 12/2007

OTHER PUBLICATIONS

Mazza et al., "A large dynamic range charge measurement ASIC family for beam monitoring in radiotherapy applications", *Nuclear Science Symposium Conference Record*, Oct. 19, 2008, pp. 1077-1080.
(Continued)

*Primary Examiner* — Christine S. Kim
(74) *Attorney, Agent, or Firm* — Nixon & Vanderhye P.C.

(57) ABSTRACT

A circuit arrangement for acquisition of signals from an apparatus for measuring beams of charged particles for external radiotherapy, in particular protons, carbon ions, and
(Continued)

other ion species, emitted by particle accelerators, comprising at least one ionization-chamber sensor (10), which includes a plurality of sensor channels (20), said circuit arrangement (200; 500) comprising a plurality of channel branches (B0, ..., B63; BR0, ..., BR63) in parallel designed to be connected to said sensor channels (20) for receiving respective measurement signals (i) therefrom, said channel branches (B0, ..., B63; BR0, ..., BR63) comprising respective current-to-frequency converters (210) and counters (220) for supplying count values (CT), representing a charge associated to a given channel (20), to a multiplexer (250; 550). According to the invention, said channel branches (BR0, ..., BR63) supply their own outputs (CT0, ..., CT63) directly to said multiplexer (550) and to an adder structure (240) comprising at least one first column ($240_1$) of adders ($241_1$) that adds up the values at the outputs (CT0, ..., CT63) of the channel branches (Br0, ..., BR63) to supply sum values (CT_100, ..., CT_115, CT_200, ..., CT_203, CT_300) at outputs thereof, said multiplexer (550) being configured for selecting, from the direct outputs (CT0, ..., CT63) of the channel branches (BR0, ..., BR63) and the outputs (CT_100, ..., CT_115, CT_200, ..., CT_203, CT_300) of the adder structure (240), a signal to be supplied to a readout electronics (400) for reading the channels (20), in particular in order to enable the channels necessary for detecting a given peak excursion via the multilayer-ionization-chamber sensor (10) without saturating.

8 Claims, 7 Drawing Sheets

(51) Int. Cl.
*A61N 5/10* (2006.01)
*G01T 1/185* (2006.01)

(56) References Cited

OTHER PUBLICATIONS

International Search Report for PCT/IB2016/053408 dated Oct. 14, 2016, 3 pages.
Written Opinion of the ISA for PCT/IB2016/053408 dated Oct. 14, 2016, 6 pages.

* cited by examiner

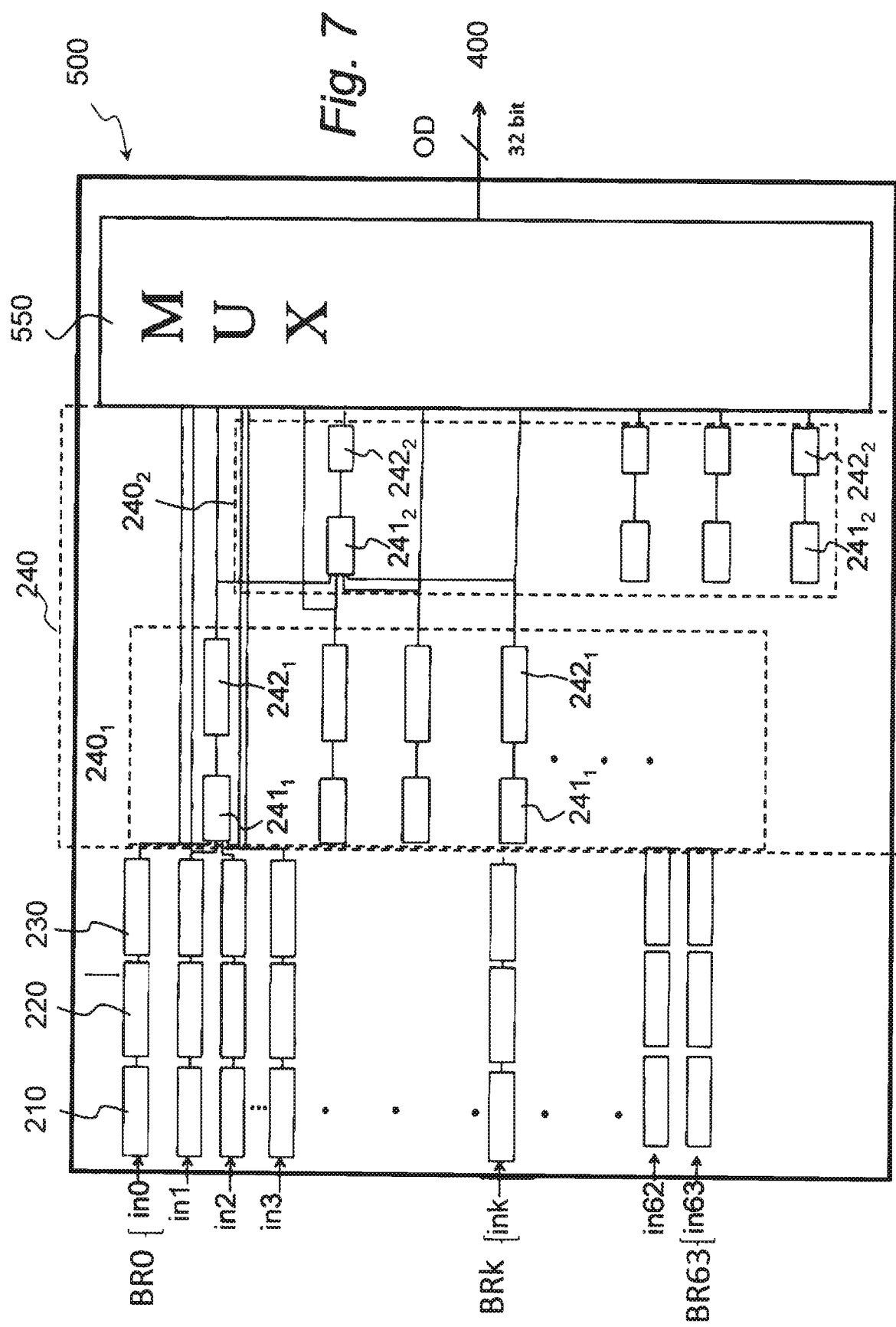

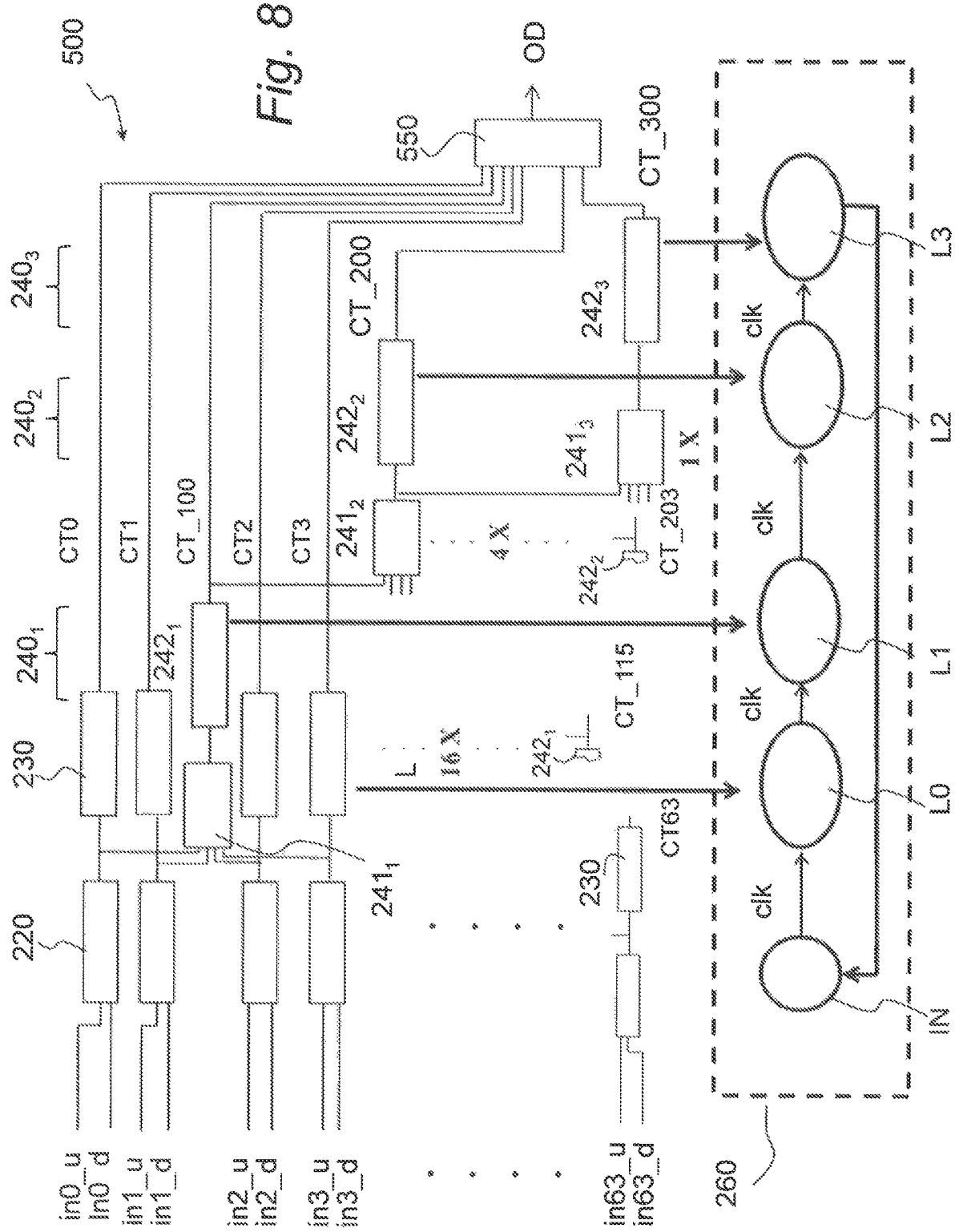

US 10,534,093 B2

CIRCUIT ARRANGEMENT FOR ACQUISITION OF SIGNALS FROM AN APPARATUS FOR MEASURING BEAMS OF CHARGED PARTICLES FOR EXTERNAL RADIOTHERAPY

This application is the U.S. national phase of International Application No. PCT/IB2016/053408 filed Jun. 9, 2016 which designated the U.S. and claims priority to IT Patent Application No. 102015000022390 filed Jun. 10, 2015, the entire contents of each of which are hereby incorporated by reference.

TECHNICAL FIELD

The present description relates to a circuit arrangement for acquisition of signals from an apparatus for measuring beams of charged particles for external radiotherapy, in particular protons, carbon ions, and other ion species, emitted by particle accelerators, comprising at least one ionization-chamber sensor, which includes a plurality of sensor channels, said circuit arrangement comprising a plurality of channel branches in parallel designed to be connected to said sensor channels for receiving input signals, said channel branches comprising respective current-to-frequency converters and counters for supplying count values, representing a charge associated to a given channel, in particular to a single parallel output, via a multiplexer.

TECHNOLOGICAL BACKGROUND

In the field of external radiotherapy with charged particles, adrotherapy, which uses protons and carbon ions and other ion species, is one of the most advanced therapies, affording a finite penetration depth, low deposition of energy at input and marked fall-off, namely, the distal decay of the distribution of the dose. However, some of its benefits may become a risk for the patient on account of the uncertainties during administration of the treatment. It is hence of fundamental importance to carry out monitoring during the radiotherapeutic treatment and regular calibration of the physical parameters of the beam of particles.

This is typically carried out by installing at output from the particle accelerator ionization chambers (with a low value of water equivalence, typically less than 1 mm) and via Quality Assurance (QA) procedures, which are carried out on a daily basis in health-care facilities equipped with different devices and instruments for each parameter to be verified.

The interaction of proton and ion beams with human tissue (which is mainly made up of water) enables the majority of the dose to be conveyed to a precise depth, following the profile of the so-called Bragg peak. In this way, it is possible to increase the precision on the target, limiting the dose that may reach healthy tissues. Moreover, the distal and lateral fall-off of a proton beam is considerably better than the lateral penumbra caused by a photon beam, enabling a fast decay of the dose in the vicinity of adjacent critical structures. As a consequence, the total energy deposited in a patient for a given target dose is lower than that of conventional treatments using photons. However, the Bragg peak for a single-energy proton and ion beam is so narrow that only a limited interval of depth can be treated with a very high dose. In order to widen the interval of treatment depth and supply a uniform dose on the tumour, a spread-out Bragg peak (SOBP) is created as set of pure peaks sent at a decreasing depth (by varying the energy of the particles) and with a reduced dose to obtain the desired modulation. FIG. 3 shows the dose DO from non-modulated proton beams (pure Bragg peak BP) and modulated proton beams (spread-out Bragg peak SOBP). It also shows the sets of peaks SP, the amplitude of which is weighted. FIG. 3 also indicates the interval EI of deposition of the energy of the spread-out peak.

Since protons and ions deposit their energy dose in a relatively small volume, corresponding to the interval EI, it is of fundamental importance to verify correctly the position of the interval EI of deposition of the beam of particles prior to treatment of patients. Calibration of the instrument (size, shape, and intensity of the beam) and verification of the depth-dose curves are carried out during the QA procedures.

According to the prior art, it is known to use for this purpose small ionization chambers or diodes that move through dummies made of tissue-equivalent materials (for example, water or perspex). In this context, it has been suggested to use multilayer ionization chambers (MLICs) in order to accelerate the QA procedures in health-care facilities, as is described, for example, in Lin, S. et al., (2009) "*A multilayer ionization chamber for proton beam Bragg peak curve measurements*", Proceedings of the International Conference of the Particle Therapy Co-Operative Group (PTCOG), Heidelberg.

The principle that superintends use of the above apparatuses is the possibility of measuring the charge deposited on each of the anodes (or cathodes) of the various layers of the device while the beam of particles passes through a stack of calibrated water-equivalent absorbers. This enables instantaneous evaluation of the depth-dose distribution of the beam (whether single-energy beam or spread-out Bragg peaks) by virtue of the simultaneous reading of all the ionization chambers that make up the MLIC device. The typical structure of an MLIC is illustrated in FIG. 1.

FIG. 1 shows in this connection an MLIC sensor 10, which comprises a plurality of sensor structures, or channels, 20, in FIG. 1 $20_1, \ldots, 20_N$, comprising pairs $15_1, \ldots, 15_N$ of anodes 11 and cathodes 12, separated by an ionization chamber 14, i.e., a space that identifies the ionization region, and followed by an absorber layer 13.

The total number of channels identifies the maximum energy range of the particles that can be measured, whereas the materials and the physical thicknesses of each channel determine the water-equivalent thickness of the MLIC sensor 10. Known MLIC sensors comprise a fixed number of channels, for example 128 or 180 channels.

FIG. 2 illustrates an accelerator 1000, which is able to generate a beam of charged particles 1300 conveyed through a tunnel 1100 and an outlet mouth 1200 in the direction of a spatial region P, which in the figure is represented as being cylindrical of a length equal to the interval EI of deposition of the energy of the spread-out peak, even though in general it may assume also other shapes. This spatial region P is located, for example, above a therapy table 1400 on which a patient to be treated can be positioned. In the spatial region P, for purposes of calibration, an apparatus for the calibration of beams of charged particles 100 is positioned in such a way that the beam of particles 1300 passes through MLIC sensors 20 that make up the calibration apparatus 100. This apparatus 100 is modular; i.e., it comprises a plurality of aligned sensor modules.

In FIG. 2 it may be noted how the modular MLIC calibration apparatus 100 comprises an outer casing 110, of a substantially parallelepipedal shape, which comprises within it a horizontal stack of modular elements 120, each including an MLIC sensor 10, or another type of sensor for measuring the position and size of the beam of particles, and a supporting frame for the aforesaid sensor.

The calibration apparatus 100 enables instantaneous evaluation of the characteristics of the therapeutic beam of particles 1300 in the directions X, Y, and Z, where Z corresponds to the direction along which the depth D is evaluated.

In this framework, where the instantaneous flow is very high and the efficiency of the calibration and measurement apparatuses must be controlled and possibly corrected, and moreover, the readout front-end of the detector and of its channels must be able to cover the entire range of expected input signals, particular attention must be dedicated to the circuit for acquisition of the signal from the channels of the detector or sensor.

Generally known are ASIC (Application-Specific Integrated Circuit) circuit solutions based upon a count-type charge converter.

These circuits comprise, in the first place, a plurality of channel circuits. Each channel circuit converts the input charge into an increment of a given number of counts of a purposely provided counter, where a fixed amount of charge, in what follows referred to as "quantum of charge", corresponds to the count of one.

A schematic representation of a channel circuit 205 is shown in FIG. 4.

An input current i is integrated by means of an integrator circuit 201 comprising an operational transconductance amplifier (OTA) 202, an input resistance Rin connected to the inverting terminal of the OTA 202, and a capacitance Cint between the inverting terminal and the output of the OTA 202. An output voltage Vout of the integrator 201, at output from the OTA 202, increases when the input current i is negative, i.e., it comes out of the channel circuit 205, whereas it decreases otherwise. The output voltage Vout of the integrator 201 is compared with two fixed thresholds, a high one VTH and a low one VTL, via two synchronous comparators CMP_1 and CMP_2, the other input of which is connected to the output voltage Vout of the integrator 201. The threshold voltage of each of the two comparators CMP_1 and CMP_2 is set from outside: the high threshold voltage VTH is the voltage threshold of the first comparator CMP_1 that operates on negative input currents i, whereas the low threshold voltage VTL regards the comparator CMP_2, which is active for positive input currents. The value of the thresholds VTH and VTL does not have a particular influence on operation of the channel circuit 205 as long as the voltage variation remains within the output range of the OTA 202 and as long as the difference VTH-VTL between the two thresholds is greater than the voltage jump caused by subtraction of the charge quantum.

The comparators CMP_1 and CMP_2 have their own outputs connected to two control inputs of a pulse generator PG. Appearing in FIG. 4 is also a periodic clock signal clk, which provides a synchronisation reference both to the comparators CMP_1 and CMP_2 and to the pulse generator PG.

The input node A of the OTA 202 is connected to a reference voltage VR, which is also the node on which the current pulse of polarity opposite to the one used for subtraction of charge is discharged, operating through two switches in series, a first switch sw1 and a second switch sw2.

The reference voltage VR is a voltage that is connected to guard rings in the sensor to ensure that any possible charges that are not directly generated by ionization, but are for example generated by the difference of potential present between layers, are collected by the guard rings, without being transmitted to the layer on which the measurement signal (i.e., the current i) is picked up, which thus collects prevalently just the charges produced by ionization of the gas traversed by the beam of charged particles.

The channel circuit 205 further comprises a charge-control capacitance Csub, one terminal of which is connected to the node identified between the first switch sw and the second switch sw2.

Whenever the input voltage of the comparator CMP_1 or CMP_2, i.e., the output voltage Vout of the integrator 201, crosses the respective threshold VTH or VTL, the corresponding comparator CMP_1 or CMP_2 sets at its output a given logic level for the input of a pulse generator PG. As long as this input level is set, the pulse generator PG sends to a capacitor Csub a positive pulse PC on its other terminal, as shown in FIG. 5. The voltage amplitude of the pulse PC, $\Delta V pulse$, is defined as the difference between two reference voltages Vp+ and Vp−, which are set from outside.

The total capacitance Csub may be obtained with three capacitors in parallel, of 50, 100, and 200 fF respectively, which may be added independently, so that the charge-control capacitance Csub can be selected with each value between 50 and 350 fF in steps of 50 fF, via a capacitance-selection signal Cap_sel. The output response of the capacitance Csub to a voltage pulse PC is represented by two current signals of opposite sign, $\delta+$ and $\delta-$, associated to which are charges Q+ and Q−, respectively, according to the following relation (1):

$$Q+ = C sub \cdot \Delta V pulse$$

$$Q- = C sub \cdot (-\Delta V pulse) \qquad (1)$$

The timing of the first current signal $\delta+$ is determined by the rising edge of the pulse PC, whereas the negative current signal $\delta-$ corresponds to the falling edge of the pulse.

By operating on the timing of the command pulses P1 and P2 of the switches sw1 and sw2, the charge Q+ or Q− can be directed either to the input of the OTA 202 or else to the reference voltage VR, adding or subtracting a fixed amount of charge at each pulse P1, P2 generated by the pulse generator PG. The decision on which of the charge signals is to be sent to the OTA 202 depends upon the output of the comparators, in order to remove a fixed amount of charge from the capacitor Cint of the integrator. This results in a change in the voltage drop on the capacitor Cint, which is given by Q/Cint.

FIG. 5 shows a timing chart that represents the pulse PC sent to the capacitor Csub, the command pulses P1, P2 of the switches sw1, sw2, and the currents $\delta+$ and $\delta-$ in the switches.

If, after the action described above, the input voltage, i.e., the output Vout of the integrator 201 of the comparator CMP_1 (or CMP_2) remains above (below) the threshold VTH (or VTL), the pulse generator PG continues to emit pulses PC and stops when the voltage Vout passes again below (above) the threshold.

In parallel, the pulse generator PG sends a count pulse, which may be a signal for increment Cnt_Up or a signal for decrement Cnt_Down of the up/down counter 220, according to which is the comparator that is acting at its input.

All the operations are synchronized via the external master clock clk and controlled via a digital finite-state machine (FSM) implemented in the generator block PG and not shown in FIG. 4. If at a cycle of the clock signal the pulse generator PG detects that the comparator CMP_1 (or CMP_2) is active, the next two clock cycles are used for generating the pulses for charge subtraction and command of the switches sw1/sw2. Two supplementary clock cycles are required before re-activation of the FSM in the pulse generator PG in order to leave time for the OTA 202 to reduce the output voltage. Thus, to generate a count, five master-clock pulses are required.

The relation between the frequency of counts ν and the input current i is:

$$v = \frac{i}{Q_c} \quad (2)$$

where $Q_c$ is the quantum of charge, which is given by:

$$Q_c = C_{sub} \cdot \Delta V pulse \quad (3)$$

Reading of the total charge collected in the detector is provided by the number of counts generated during the measurement time multiplied by the value of the charge quantum $Q_c$.

FIG. 6 shows a known solution of circuit arrangement, designated by 200, which envisages operating, for example, with a measurement apparatus 100 that has available a number M of channels 20 comprised in one or more MLIC sensors 10 arranged in a horizontal stack, as described with reference to FIG. 2. It is here emphasized how reference to a sensor 10 of an MLIC type is provided purely by way of non-limiting example, it being possible for the sensor to be also of some other ionization-chamber type suitable for detecting the intensity of beams of charged particles and configured for sending its own measurement signal through a plurality of measurement channels 20, for example a pixel ionization-chamber detector. The circuit arrangement 200 comprises a number N equal to 64 of inputs in0, . . . , in63, on each of which a channel 20 can be connected for conveying thereto a corresponding current i collected by the channel 20 of the MLIC sensor 10.

Each of the above inputs in0, . . . , in63 in the circuit arrangement 200 is the input of a respective circuit branch B0, . . . , B63. Each k-th branch Bk comprises a channel conversion circuit 205 including a respective current-to-frequency converter 210, which converts the respective current i at input to the k-th branch into a frequency $v_k$. This frequency $v_k$ is then measured by a counter 220, comprised in the k-th branch Bk, which supplies at output the value of the counter CT, in particular a 32-bit value.

The values assumed by the counters CT0, . . . , CT63 of the branches B0, . . . , B63 are supplied as inputs to a multiplexer 250, which, upon command from a 6-bit selection bus CS, enables selection of the channel 20 from the channels connected to the inputs in0, . . . , in63, i.e., of the branch from the branches B0, . . . , B63, to be sent at its own output as output data O and to be acquired via a readout electronics 400 not shown in FIG. 4. It should be noted that, in effect, the current-to-frequency converter implemented by the circuit arrangement 200 corresponds to a charge-to-count converter.

As may be noted, in the circuit arrangement 200 of FIG. 4 also shown at input are the signals, supplied by an external controller, that have the function of controlling the channel circuits 205, hence the thresholds VTH, VTL of the comparators, the voltages VP+, VP−, the capacitance-selection signal Cap_sel, in addition to the signal on the selection bus CS of the chip and the selection circuits of the multiplexer 250. The circuit 200 moreover receives a latch signal, L, which has the function of loading at a given instant the output of the counters 220 into as many registers, and moreover an integrator-reset signal RA and a counter-reset signal RD. The integration capacitor Cint of each channel circuit 205 may in fact be discharged through a common digital reset input RA. Likewise, all the counters 220 may be zeroed via a common reset asynchronous digital input, RD.

The circuit of FIG. 4 is described, for example, in the paper by La Rosa et al., Nuclear Instruments and Methods in Physics Research A 583 (2007) 461-468 and manages, via a single channel branch, a respective channel.

However, in this type of circuit, even using a maximum conversion rate of 20 MHz and configuring the quantum of charge to the maximum value (for example, 1.155 pC), the maximum current that a branch can convert before saturating is less than 24 μA. This value is too low for applications with pulsed accelerators, such as synchrocyclotrons. With these instruments, with a duty cycle of the pulse of a few units per thousand, the instantaneous current during the pulse must reach values greater than those of current applications with linear accelerators, even by two or three orders of magnitude.

Consequently, the known solutions present limits in the values of amplitude of current on the channels that they can manage.

OBJECT AND SUMMARY

The object of embodiments described herein is to improve the apparatuses and methods according to the known art as discussed previously.

Various embodiments achieve the above object thanks to a circuit arrangement having the characteristics recalled in the ensuing claims.

Various embodiments also refer to a corresponding measurement apparatus and method.

The claims form an integral part of the technical teachings provided herein in relation to the invention.

BRIEF DESCRIPTION OF THE DRAWINGS

Various embodiments will now be described, purely by way of example, with reference to the annexed drawings, wherein:

FIG. 7 shows a principle circuit diagram of the circuit arrangement described;

FIG. 8 shows a diagram representing the circuit arrangement described and corresponding control signals.

DETAILED DESCRIPTION

In the ensuing description, numerous specific details are provided in order to enable maximum understanding of the embodiments provided by way of example. The embodiments may be implemented with or without specific details or else with other methods, components, materials, etc. In other circumstances, well-known structures, materials, or operations are not illustrated or described in detail so that aspects of the embodiments will not be obscured. Reference, in the course of the present description, to "an embodiment" or "one embodiment" is meant to indicate that a particular structure, feature, or characteristic described in connection with the embodiment is comprised in at least one embodiment. Hence, phrases such as "in an embodiment", "in one embodiment", or the like, that may appear in various points of this description do not necessarily refer to one and the same embodiment. Moreover, the particular structures, features, or characteristics may be combined in any convenient way in one or more embodiments.

The notation and references are provided herein only for convenience of the reader and do not define the sphere of protection or the scope of the embodiments.

In brief, the circuit arrangement proposed herein envisages providing, for a plurality of channels, a plurality of channel circuits comprising current-to-frequency converters and counters for supplying a respective channel count, stored in a respective channel register, as well as an adder-tree structure comprising at least one first column, or row, of adders that adds up the outputs of sets of channel registers, in particular comprising further columns of adders that add up the outputs, which are, in particular, stored in respective registers of the adders, of the adders of the previous column. The outputs of the channel registers and of each adder of each column are supplied to a multiplexer, which can in this way enable the channels necessary for detecting a given peak excursion without saturating.

FIG. 7 shows an embodiment 500 of a circuit arrangement for acquisition of signals from an apparatus for calibration of beams of charged particles for external radiotherapy according to the invention.

Figure 1:
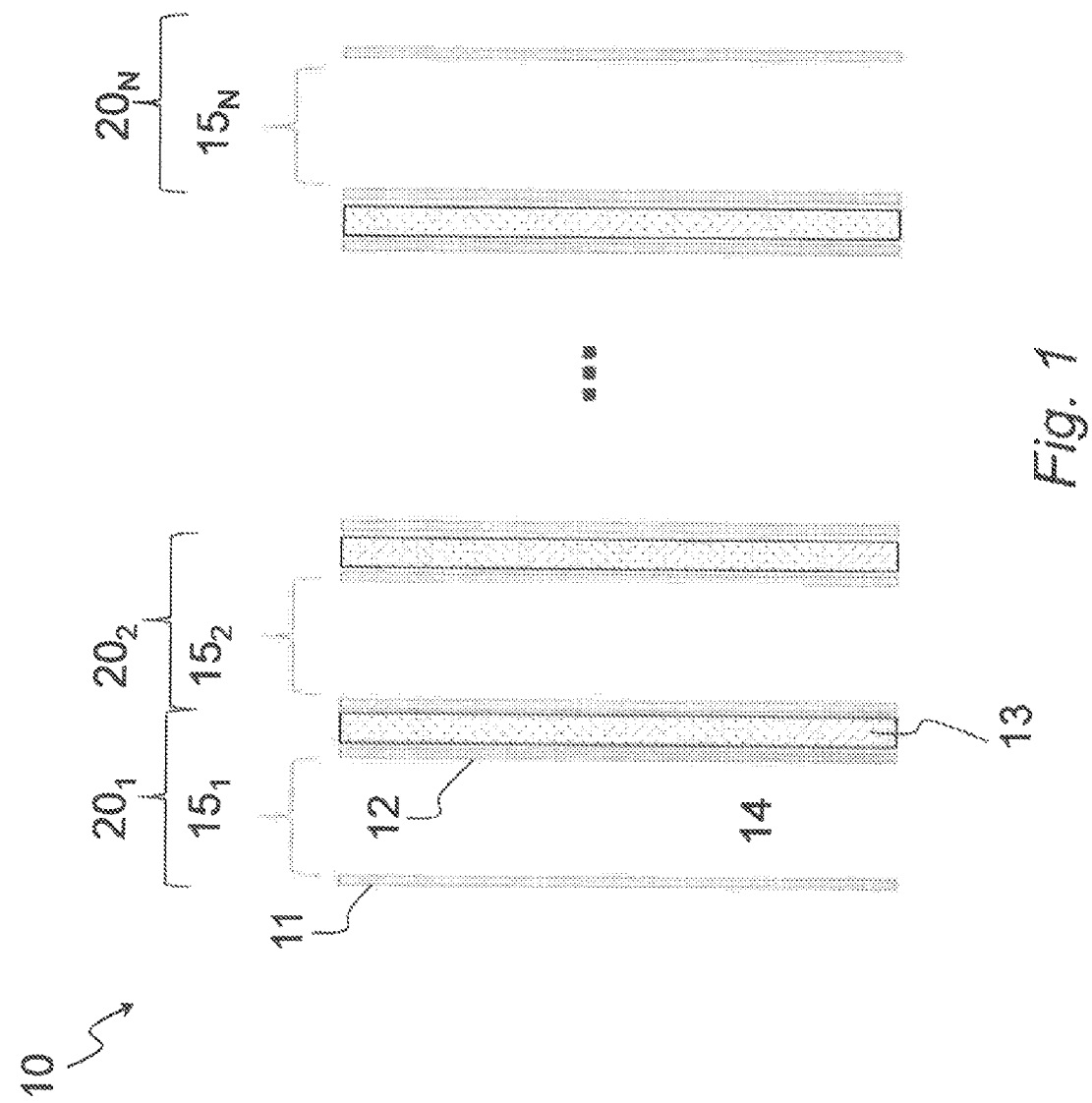
FIG. 1 shows the typical structure of an MLIC.
Figure 2:
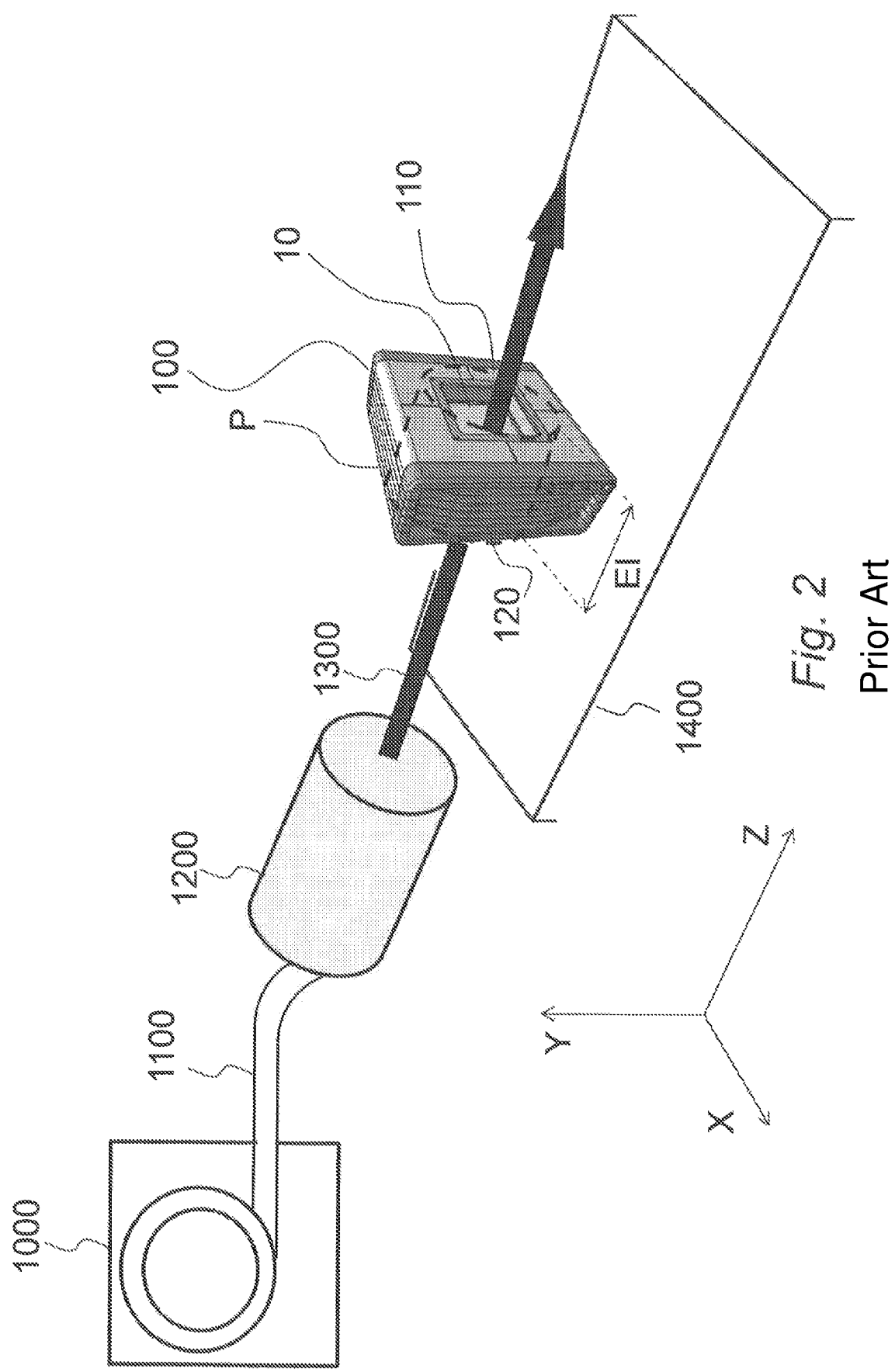
FIG. 2 illustrates an accelerator.
Figure 3:
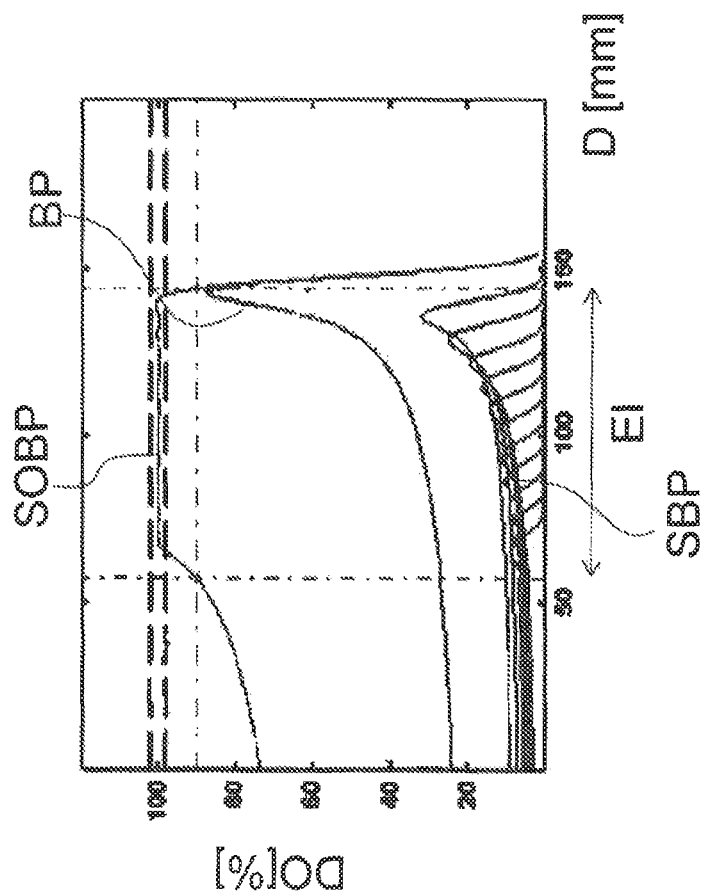
FIG. 3 shows the dose DO from non-modulated proton beams (pure Bragg peak BP) and modulated proton beams (spread-out Bragg peak SOBP)
Figure 4:
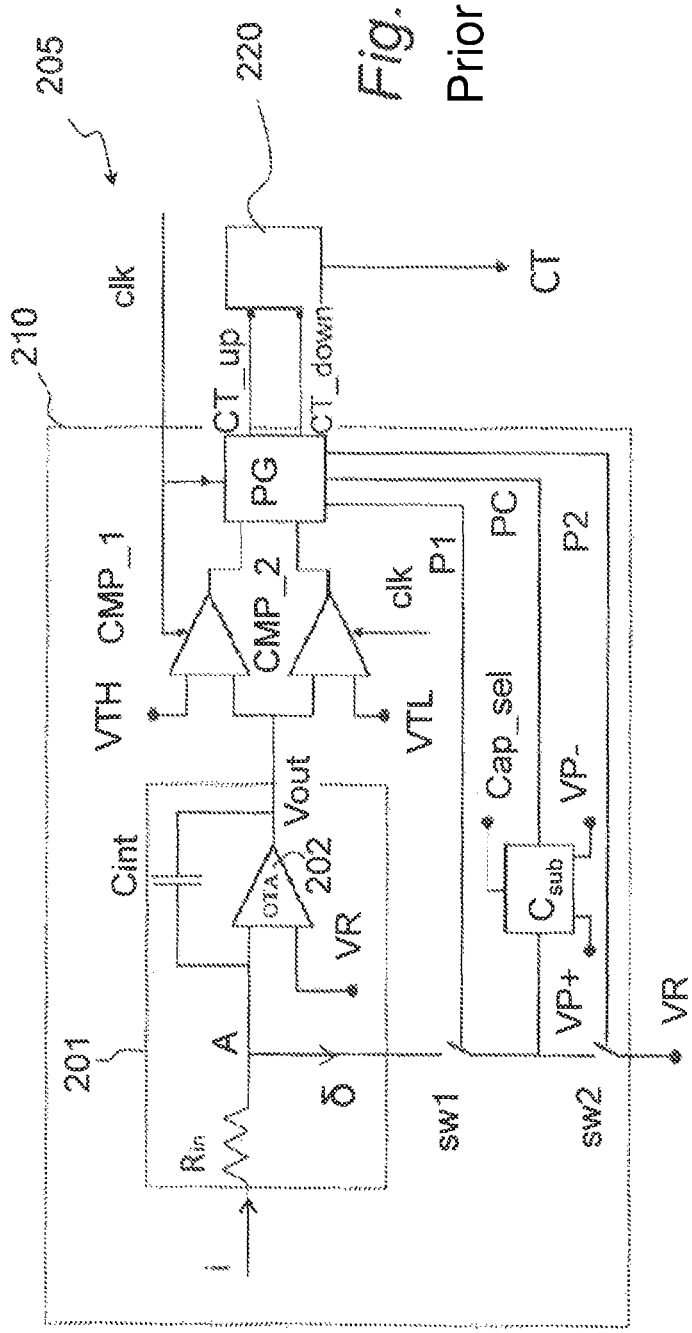
FIG. 4 shows a schematic representation of a channel circuit.
Figure 5:
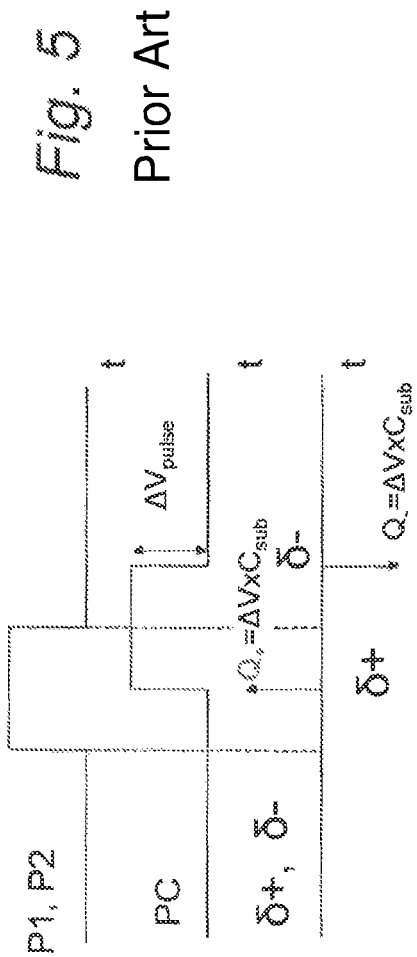
FIG. 5 shows a timing chart that re resents the pulse PC sent to the capacitor Csub, the command pulses P1, P2 of the switches sw1, sw2, and the currents δ+ and δ− in the switches.

As may be seen in FIG. 7, the architecture of the above circuit arrangement 500 comprises a plurality of branches BR0, ..., BR63 for the plurality of inputs in0, ..., in63, it being possible for each to be connected to a measurement channel 20 of an ionization-chamber sensor 10 in order to receive a respective measurement signal, in particular a current signal. Each k-th branch BRK comprises a channel circuit 205, like the one shown in FIG. 4, hence comprising a voltage-to-frequency converter 210 and a counter 220, as well as a channel register 230. Also in this case the current-to-frequency converter implemented by the circuit arrangement 500 corresponds, in actual fact, to a charge-to-count converter.

Figure 6:
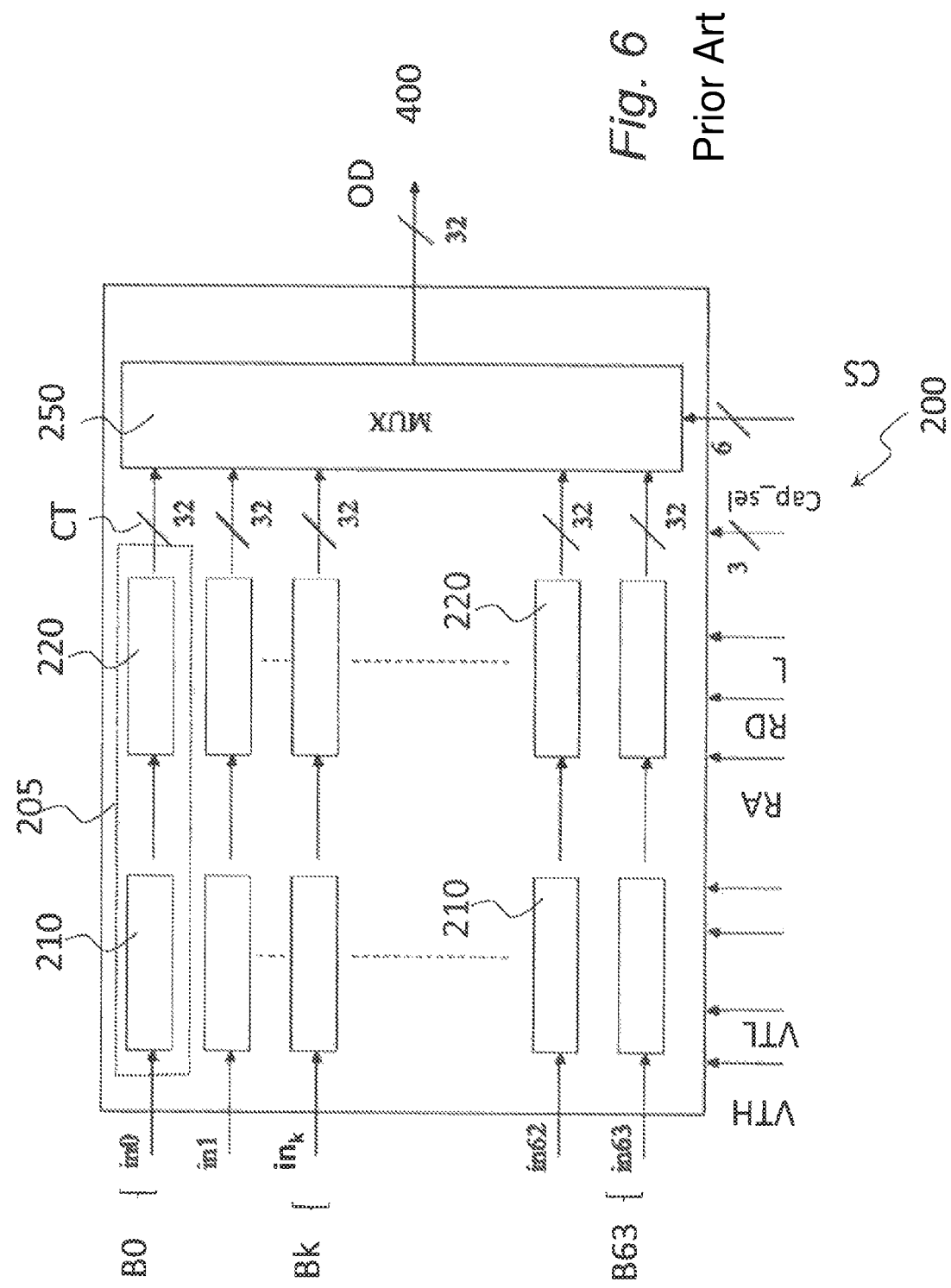
FIG. 6 shows a known solution of circuit arrangement.

Unlike the circuit arrangement 200 of FIG. 6, the plurality of branches BR0, ..., BR63 are connected to a multiplexer 550 either directly, i.e., the N=64 outputs, which are the values of the counters CT0, ..., CT63, of the channel registers 230 are connected to 64 inputs of the multiplexer 550, or through an adder structure 240. The adder structure 240 receives at input the outputs, or count values, CT0, ..., CT63, of the channel branches BR0, ..., BR63. Each channel branch BRk receives a measurement signal, in particular a current, at its input ink, determined by the connection to this input ink of the measurement channel 20, and supplies an output, i.e., a corresponding count CT. As discussed hereinafter, one measurement channel 20 can be connected to a number of inputs of the circuit arrangement 500; hence, an input ink may not receive the entire current of a channel 20. The adder structure 240 supplies at output sums of the measurement signals present at the inputs in0, ..., in63, or at a part of the inputs in0, ..., in63. In particular, the adder structure 240 supplies at output the data coming from sums of counts corresponding to the sum of:

sets of four inputs, the sixteen signals CT_100, ..., CT_115;
sets of sixteen inputs, the four signals CT_200, ..., CT_203;
sum CT_300 of all the counts corresponding to all the 64 inputs at input to the circuit arrangement 500.

In this way, it is possible to extend the current range at input to the circuit arrangement 500 from a few microamps to hundreds of microamps, simply by selecting one of the addresses of the multiplexer 550 and connecting in parallel the set of inputs the sum of which is contained in that address. In particular, as will be discussed in greater detail in what follows, one of the addresses is selected corresponding to a sum of a number of inputs ink for one and the same measurement channel 20 that are such as to divide the current on each of the aforesaid inputs below a saturation value. The direct signals CT0, ..., CT63, and sum signals CT_100, ..., CT_115, CT_200, ..., CT_203, CT_300 at input to the multiplexer 550 are shown in FIG. 8. The multiplexer 550 in this way has 85 inputs: 64 inputs from the individual channels, 16 inputs as sum of four channel branches, 4 inputs as sum of 16 channel branches (sum of four which are sum of four) and one input as sum of all the channel branches (sum of four which are sum of sixteen), which is not shown in FIG. 7 and is in part visible in FIG. 8.

In greater detail, the adder structure 240 comprises an adder-tree structure including a first column $240_1$, or row, of adders $241_1$ that adds up the outputs of sets of channel registers 230, specifically sets of four channel registers 230, and stores the result of the sum in a respective sum register $242_1$.

The adder system 240 comprises further columns of adders $240_i$, specifically, in the example, two further columns of adders $240_2$ and $240_3$, which add up the outputs, in particular stored in the respective registers of the adders $242_i$, of the adders $241_{i-1}$ of the previous column $240_{i-1}$. Hence, in the circuit arrangement 500, the outputs of the sixteen registers $230_1$ of the first column of the adders $241_1$ are supplied four by four to the four adders $241_2$ of the second column $240_2$. The outputs of the four registers $230_2$ of the second column of the adders $241_2$ are supplied to a single adder $241_3$ of the third column $240_3$. It is clear how the number of columns of adders and the number of adders in each column may be set even in a different way, according to the characteristics of the signals of the channels and of the measurement apparatus. The outputs of the first, second, and third column of adders are supplied to the multiplexer 550, which can, in this way, under the control of the selection signal 550, enable the channel branches necessary for detecting a given peak excursion without saturating.

As already anticipated, FIG. 8 is a partial representation. In fact, it shows only the structure that, starting from the first four signals CT0, ..., CT3, generates the sum signal CT_100 at output from the adder $242_1$, as well as the path of the sum signal CT_100 in order to generate the sum signals CT_200 and CT-300, through subsequent adders $242_1$ and $242_3$. As regards the remaining direct signals CT0, ..., CT63 and sum signals CT_100, ..., CT_115, CT_200, ..., CT_203, CT_300, only the last signals CT63, CT_115, CT_203 are indicated in a schematic principle representation.

The circuit arrangement 500 is hence used as follows: in the case where on a given channel 20 of a sensor 10 a current is expected such as to saturate the single branch Bk, for example a current with a value that is twice the saturation current that can be withstood by the single branch Bk, the channel 20 is connected in parallel to a plurality of branches; for example, the signal of a given channel 20 is connected to the branches B0, . . . , B3 so that the current is divided on the four branches B0, . . . , B3, thus preventing saturation of the channel circuits. In this case, the multiplexer 550 is configured for selecting, for the given channel 20, the output CT100 of the first column $240_1$ of adders $241_1$. It is clear that, if, also other channels 20 are expected to have a current that is twice the saturation current, these are connected to other sets of branches that come under one and the same adder 241. Likewise, if the current supplied is higher, such as to saturate a channel circuit 205 even if the current is divided by four, it is possible connect the same given channel 20 to sixteen branches grouped in one and the same adder of the second column (selecting the output CT_200 in the multiplexer 550) or even, in the case of a much higher current, it is possible to connect the same given channel 20 to all sixty-four branches B0, . . . , B63, selecting the output that adds up all the branches, CT_300.

In other words, the circuit arrangement 200 comprises inputs in0, . . . , in63 pre-arranged for being connected in sets of two or more at output from a measurement channel 20 that supplies a measurement signal i. This arrangement may take on, for example, the form of a simple electrical connection between the output of the measurement channel 20 and a set of the inputs in0, . . . , ink, for example via an input terminal, or common node, connected at output from the measurement channel 20, departing from which are electrical cables or wires in parallel connected, either directly or via passive elements such as electrical resistances, to the respective inputs of the set. The cables or wires may, in particular, be connected manually, in so far as in general the measuring time does not entail the need to modify in an automated way the connections of the signals of the measurement channels 20 to the inputs in0, . . . , ink of the circuit arrangement 200. It is, however, also possible to have, alternatively, a demultiplexer structure, which receives at input a measurement signal of one channel 20 and connects it, under the control of a respective control signal, governed for example by a computer, to a single input or else to two or more inputs in0, . . . , ink in parallel. This control signal of the demultiplexer can hence be co-ordinated with the selection signal of the multiplexer 550 to connect simultaneously one measurement signal to a set of inputs and to select the output of the multiplexer corresponding to the sum of the set of branches BR0, . . . , BRK corresponding to the set of inputs in0, . . . , ink. Hence, it is possible to use a manual or automatic electrical connection arrangement for connecting a sensor channel 20 to a set of inputs of the plurality of inputs in0, . . . , ink of the device 200.

Hence, more in general, an apparatus is provided for measurement of beams of charged particles for external radiotherapy, which comprises at least one sensor channel or measurement channel 20, the output of which is connected, in particular via a manual or automatic electrical connection arrangement, in parallel to at least one set of inputs in the plurality in0, . . . , ink of the circuit arrangement 500 (or 200), and the multiplexer 550 is configured for selecting the outputs CT_100, . . . , CT_115, or CT_200, . . . , CT_203 or CT_300 of the adder structure 240 that adds up the values to the outputs CT0, . . . , CT63 of the channel branches BR0, . . . , BR63 corresponding to the set of inputs in0, . . . , ink and for supplying them to the channel-readout circuit.

It should be noted in this context, where a number of channels are connected together at the input of the OTA, the input resistance Rin on the channel circuit 205 is particularly useful.

Hence, it is envisaged more in general to carry out, via the circuit arrangement 500, a measurement method that comprises connecting a given channel 20 of a sensor 10 to a respective branch or to a set of branches BR0, . . . , BR63, in the example it being possible for the set to comprise four, sixteen, or sixty-four adjacent branches, of the circuit arrangement 500 that converges into one or more columns, in particular $240_1$, $240_2$, or $240_3$ of adders 241 as a function of the value of a maximum current expected on that channel 20 of the sensor 10, configuring, via a 7-bit selection bus, the multiplexer 550 to select an output, corresponding to connection of that given channel 20, from among the direct outputs CT0, . . . , CT63 of the channel branches BR0, . . . , BR63 and the outputs CT_100, . . . , CT_115, CT_200, . . . , CT_203, CT_300 (i.e., the outputs of the respective sets of four, sixteen, and sixty-four adjacent branches) of the adder structure 240, as signal to be supplied to a readout electronics 400 for reading of the channels 20. In particular, the operation of connecting a given channel 20 of a sensor 10 to a respective branch or to a set of branches of the circuit arrangement 500 comprises selecting for the connection a set of branches having a number of branches, in the example four, sixteen, or sixty-four, such as to divide on each branch a current lower than a saturation current of the channel circuit 205.

Note that the third column $240_3$ is not shown in FIG. 7, whereas it is shown in FIG. 8.

Reading of the counters 230 can be carried out independently from any other operation.

FIG. 8 shows the circuit arrangement 500 in association with a further finite-state machine 260 of a Moore type that manages a loading signal L, which regulates storage of the 32-bit registers, i.e., the register 230 of the counter 220 and the registers $242_i$ of each i-th column $240_i$ of adders $241_i$. The circuit 500 is shown only in part without the channel circuit 210. Consequently, for each k-th channel $in_k$, signals ink_u and ink_d are represented that correspond to the count signals cnt_up and cnt_down of FIG. 4. The loading signal L is shifted synchronously with the clock clk: in the example illustrated in FIG. 8, first, after an initial state IN, at the first clock tick clk control of the FSM passes to a state L0, where the channel registers 230 connected to the counters 220 are loaded with the output, i.e., the total number counts CT thereof. Then, at a next clock tick clk control passes to a next state L1 where the registers $242_1$ of the first column $240_1$ are loaded with the sum of the respective adders $242_1$, i.e., of four channels; then (state L2) the registers $240_2$ of the second column $240_2$, which contain the sum of sixteen channels, are loaded; finally (state L3) the register $242_3$ that contains the sum of the N=64 channels is loaded. Control in the finite-state machine 260 then returns to the initial state IN. In this way, it is possible to reduce the propagation time necessary before an operation of storage in the registers 230, 242, which has to be made by circuit arrangement 500, can be carried out, instead of simply loading all the 85 registers 230, $242_i$, of the circuit at each clock pulse clk.

It should be noted that the latch operation between the output of the counter and the input of the register, i.e., of storage, takes place simultaneously for all the channels: the contents of the counters are copied into the registers, once the count transitions are through.

Moreover, even though the acquisition must be carried out channel by channel, the counters are stored in the registers all at the same time. Thus, once the cycle of the state machine 260 is through, the data in the registers 230 and 242 refer to the same time.

Since the operation of acquisition is independent of the count of the pulses, the acquisition of the data does not stop the activity of the counter 220, and hence there is no dead time on account of readout of the channels.

Each register 230 and 242 of the circuit arrangement 500 has available a single bit of alarm signal that is activated when the most-significant bit of the counter (for a positive number and accordingly in two's complement for negative numbers), passes from 0 to 1. When an OR logic that has as inputs all the signals corresponding to the various registers of the structure is equal to 1, an operation of asynchronous reset can be used for unloading the registers in order to prevent overflow and hence loss of data. In particular, the OR gate collects the alarm signal of all the registers 230 and 242 and indicates that one of the registers has exceeded half of its maximum capacity. It then enables the readout electronics for sending a reset signal before overflow is reached.

The circuit arrangement 500 described operates, for example, at a clock frequency of 400 MHz and at a maximum conversion rate of 80 MHz, the charge quantum Qc being selected in a range between 50 fC and 350 fC, thus enabling the limits of current of prior-art circuits to be overcome.

Hence, from what has been described, the solution and the corresponding advantages emerge clearly.

The circuit arrangement described, thanks to the architecture that joins branches in parallel for each channel to an adder structure set between the branches and the multiplexer, enables the limits of current of known circuits to be overcome.

The solution described herein makes it possible to obtain a uniform channel-to-channel relative gain, i.e., the gain of one channel with respect to the other, linearity over a wide dynamic range, and negligible background currents, as well as the possibility of managing a wider dynamic range of input currents, of the order of $10^4$. To obtain these targets, a technology with large scale of integration is used, 0.35-μm CMOS technology, in implementation of the ASIC, which enables installation of the chips in the proximity of the detector.

The solution described herein can operate with inputs of both polarities, using 32-bit synchronous counters with up/down count capacity. In this way, the charge can be measured by counting the pulses at output from the channel converter in a given time interval. The output of the channel circuit is hence already in digital format, which enables a simpler subsequent management of the data.

The circuit arrangement described operates at a clock frequency of 400 MHz and a maximum conversion rate of 80 MHz. The conversion of bipolar inputs makes it possible to extend the application of the circuit arrangement described to all the detectors that are used in the technical sector of calibration of beams of charged particles, and moreover enables a better precision in the measurement of low-current regimes (of the order of picoamps).

Of course, without prejudice to the principle of the invention, the details and the embodiments may vary, even considerably, with respect to what has been described herein purely by way of example, without thereby departing from the sphere of protection, which is defined by the annexed claims.

The circuit arrangement described can operate with the ionization-chamber sensors that envisage channels arranged in a stack that develops along the direction of the beam, but can also operate with two-dimensional sensors, known as "pixel ionization-chamber detectors", which comprise an array of cells or pixels in the plane orthogonal to the beam, each of which corresponds to a channel and is hence designed to supply a current proportional to the dose that impinges on that cell or pixel, and in any case with all the ionization-chamber sensors suitable for detecting the intensity of beams of charged particles and configured for sending their own measurement signal through a plurality of measurement channels.

The invention claimed is:

1. A circuit arrangement for acquisition of signals from an apparatus for measuring beams of charged particles for external radiotherapy, emitted by particle accelerators, the circuit arrangement comprising at least one ionization-chamber sensor, said at least one ionization-chamber sensor comprising a plurality of sensor channels, said circuit arrangement comprising a plurality of channel branches in parallel designed to be connected to said sensor channels for receiving respective measurement signals therefrom, said channel branches comprising respective current-to-frequency converters and counters for supplying count values, representing a charge associated to a given channel, to a multiplexer comprised in said circuit arrangement,
said circuit arrangement comprising an adder structure including at least one first column of adders that adds up the count values at the outputs of the channel branches for supplying sum values at outputs thereof;
said circuit arrangement being further configured to connect a given channel of the sensor to a respective channel branch or to a set of channel branches that converges into said at least one first column of adders as a function of the value of a maximum current expected on said channel of the sensor;
said channel branches supply their own outputs to said adder structure and directly to said multiplexer, and, said multiplexer being configured for selecting, from the direct outputs of the channel branches and the outputs of the adder structure, a signal to be supplied to a readout electronics, for reading of the channels.

2. The circuit arrangement according to claim 1, wherein it comprises one or more further columns of adders that add up outputs of the adders of a previous column to form further outputs of the adder structure connected to the inputs of said multiplexer.

3. The circuit arrangement according to claim 1, wherein each channel branch comprises a respective channel register connected for storing the value of count of the counter, and each adder is associated to a respective adder register for storing the value of count of the adder.

4. The circuit arrangement according to claim 3, wherein it comprises a finite-state machine configured for storing data in the channel registers and in the registers of the adders of each column synchronously with a clock signal, at each tick of the clock signal storing data in sequence in the channel register or in each subsequent column of adders.

5. The circuit arrangement according to claim 3, wherein each channel register and adder register has available an alarm signal that is activated when a most-significant bit of the digital value of the counter passes to high logic level, and a logic circuit, which receives at input each signal of each channel register and adder register configured for verifying whether all said alarm signals are at a high level and accordingly issuing a command, for an operation of asynchronous reset for unloading said channel and adder registers in order to prevent a state of overflow.

6. An apparatus for measuring beams of charged particles for external radiotherapy comprising a circuit for readout of the channels comprising a circuit arrangement according to claim 1.

7. A method for measuring beams of charged particles, emitted by systems for external radiotherapy with charged particles that uses a measurement apparatus according to claim 6, including connecting the given channel of the sensor to the respective channel branch or to the set of channel branches of said circuit arrangement that converges into one or more columns of adders as a function of the value of the maximum current expected on the channel of the sensor;

configuring said multiplexer for selecting the output, corresponding to the connection of said given channel, from among the direct outputs of the channel branches and the outputs of the adder structure, as signal to be supplied to the readout electronics for reading of the channels.

8. The method according to claim 7, wherein said operation of connecting the given channel of the sensor to the respective branch or set of branches of said circuit arrangement comprises selecting, for the connection, the set of branches having a number of branches such as to divide on each branch a current lower than the current of saturation of the channel circuit.

\* \* \* \* \*